(12) United States Patent
Stephien et al.

(10) Patent No.: US 9,375,492 B2
(45) Date of Patent: Jun. 28, 2016

(54) MIXTURE OF LIQUID-CRYSTAL COMPOUNDS, SYSTEM OF THREE LIQUID-CRYSTAL MIXTURES AND THEIR USE

(71) Applicant: BRASTER SA, Szeligi (PL)

(72) Inventors: Jacek Bernard Stephien, Warsaw (PL); Henryk Jaremek, Warsaw (PL); Grzegorz Franciszek Pielak, Serock (PL)

(73) Assignee: BRASTER SA, Szeligi (PL)

( * ) Notice: Subject to any disclaimer, the term of this patent is extended or adjusted under 35 U.S.C. 154(b) by 238 days.

(21) Appl. No.: 14/038,491

(22) Filed: Sep. 26, 2013

(65) Prior Publication Data

US 2014/0037546 A1 Feb. 6, 2014

Related U.S. Application Data

(63) Continuation of application No. 13/575,827, filed as application No. PCT/PL2011/005005 on Jan. 28, 2011, now Pat. No. 8,574,457.

(30) Foreign Application Priority Data

Jan. 29, 2010 (PL) .................... PL390320

(51) Int. Cl.
| | |
|---|---|
| *C09K 19/26* | (2006.01) |
| *G01K 11/16* | (2006.01) |
| *C09K 19/54* | (2006.01) |
| *A61B 5/01* | (2006.01) |
| *A61K 49/00* | (2006.01) |
| *C09K 19/36* | (2006.01) |

(52) U.S. Cl.
CPC ............... *A61K 49/00* (2013.01); *C09K 19/26* (2013.01); *C09K 19/36* (2013.01); *G01K 11/165* (2013.01)

(58) Field of Classification Search
CPC ...... A61K 49/00; G01K 11/165; G01K 11/12
See application file for complete search history.

(56) References Cited

U.S. PATENT DOCUMENTS

| | | | | |
|---|---|---|---|---|
| 3,847,139 A * | 11/1974 | Flam | ................. | A61B 5/015 349/199 |
| 3,907,768 A * | 9/1975 | van der Veen | .......... | C07C 45/46 349/153 |
| 4,043,324 A * | 8/1977 | Shaw, IV | ............... | A61B 5/015 349/20 |
| 4,301,023 A * | 11/1981 | Schuberth | ............ | A61K 8/0295 252/299.7 |
| 4,354,385 A * | 10/1982 | Fraschini | ............. | G01K 11/165 116/216 |
| 4,433,637 A * | 2/1984 | Buirley | ................ | A61B 5/015 116/207 |
| 4,441,508 A * | 4/1984 | Buirley | ................. | C09D 5/26 252/299.7 |
| 5,058,999 A * | 10/1991 | Davis | .................. | G01K 11/165 349/197 |
| 5,508,068 A * | 4/1996 | Nakano | ................ | C09K 19/00 252/299.01 |
| 6,086,247 A * | 7/2000 | von Hollen | ............ | A61B 5/015 374/137 |
| 6,419,636 B1 * | 7/2002 | Young | ................... | A61B 5/015 600/372 |
| 2012/0319043 A1* | 12/2012 | Stepien | ................. | C09K 19/26 252/299.7 |

\* cited by examiner

*Primary Examiner* — Sean Dougherty
(74) *Attorney, Agent, or Firm* — Maier & Maier, PLLC

(57) ABSTRACT

Three organic compounds mixtures of liquid-crystal properties, which when mixed together in a precisely determined weight ratio, may show an ability to form thermo-optically active mesophases of established, narrow range thermooptical transitions separation, every 0.5° C., in the temperature range: from 31.8° C. to 32.8° C., from 32.8° C. to 33.8° C., and from 33.8° C. to 34.8° C. and system including these mixtures. The use of these mixtures and the system containing the above mentioned mixtures for colorimetric detection of temperature differentiation on the surface of biological objects in a narrow range of temperatures.

3 Claims, No Drawings

MIXTURE OF LIQUID-CRYSTAL COMPOUNDS, SYSTEM OF THREE LIQUID-CRYSTAL MIXTURES AND THEIR USE

This application is a Continuation application of U.S. application Ser. No. 13/575,827 filed Jul. 12, 2012, now U.S. Pat. No. 8,574,457 issued on Nov. 5, 2013, which is a National Stage application of International (PCT) Application No. PCT/PL2011/050005, filed on Jan. 28, 2011, under the provisions of 35 USC 371, the contents of U.S. application Ser. No. 13/575,827 being incorporated herein by reference in their entirety.

The present invention relates to three mixtures of organic compounds having liquid-crystal properties, which are mixed together in a precisely determined weight ratio and are characterised by an ability to form a thermooptically active mesophase of a established narrow range of a thermooptical transitions separation, by 0.5° C., in a temperature range: from 31.8° C. to 32.8° C., from 32.8° C. to 33.8° C., and from 33.8° C. to 34.8° C., and to the system comprising these mixtures. The present invention also relates to the use of these mixtures and the system containing the above mentioned mixtures for colorimetric detection of a temperature differentiation on a surface of biological objects in a narrow range of temperatures.

Thermography as a diagnostic method, thus also its physiological bases, is a generally approved clinical procedure of pathological lesions imaging in mammary glands in women. Breast thermography is characterised by sensitivity and specificity on a level of the order of 90%. Breast thermography may show the first symptoms of breast cancer formation, even 10 years earlier than the lesions that are detected by other diagnostic procedures, and when it is associated with other diagnostic methods (medical examination+mammography+thermography) allows detecting 95% of early phases of breast cancer. Clinical study has indicated that breast thermography considerably increases a long-term survival rate in women due to early detection of breast cancer, even up to 61%. Pathologic thermogram can be regarded as an autonomous marker of high development risk of breast cancer, and repeated pathologic thermograms are associated with 22-times higher risk of breast cancer incidence in the future. Thermography is recommended as a diagnostic method of choice at continuous anticancer monitoring in women with a positive family history.

The physiological basis for the use of thermography in medical imaging diagnosis is a dermothermic effect based on direct mapping of different metabolism rate of pathological cells through a contour-line recording of corresponding thermic changes examined area of the patient body (also including the surface of the mammary glands). The pathological lesions may have hypo- or hyperthermic expression, in relation to the average physiological temperature, dependently on the type of observed affection that at sufficiently substantial temperature distinction allows to their distinct isolation from the area of healthy tissue. In thermograms the pathological lesions are visible as distinct focuses of reduced or increased temperature.

There are known diagnostic methods utilising remote thermography and contact thermography. In known methods of contact thermography, thermooptical effect resulting from the properties of the thermotropic mesophase of cholesteric liquid crystals is used, that is based on the change of optical rotation plane of precisely selected liquid-crystal mixture, wherein this effect is revealed at precisely determined temperature, which allows precise calibration of a colour-temperature response scale. These solutions are known inter alia from the patent specifications U.S. Pat. No. 3,847,139, GB2060879, EP0059328. However, the above mentioned solutions are unsatisfactorily particularly related to the problem of uniqueness of the thermic changes readout with certain diagnostic value through providing necessary colour distinction for individually recorded temperatures that considerably made difficult, or even made impossible their practical application.

According to the latest studies of Zhao et al. (Qi Zhao, Jiaming Zhang, Ru Wang, Wei Cong; Use of a Thermocouple for Malignant Tumor Detection; Ieee Eng. in Medicine and Biology Mag., January February 2008) thermic differentiation exceeding +0.5° C. (on the average +0.7° C.) in relation to the surrounding healthy tissue, is typical of malignant neoplastic tumours in mammary glands, allowing their indirect localisation just through the observation of anomalous focuses of increased temperature on the surface of the breast. That is why, in the art there is need for novel liquid-crystal mixtures suitable for the range imaging (every 0.5° C.) of isotherm distribution on the surface of the breast.

It is an object of the present invention to provide the liquid-crystal mixtures able to formation of the thermooptically active mesophase of established narrow range of the thermooptical transitions separation, every 0.5° C., in the temperature range: from 31.8° C. to 32.8° C., from 32.8° C. to 33.8° C., and from 33.8° C. to 34.8° C. The above object is realised by developing the composition of liquid-crystal mixtures having the required properties.

The liquid-crystal mixtures in the system according to the present invention, due to their unique length change property, thus the colour of the selectively reflected light in the mesophase, precisely every 0.5° C., in a very narrow range of thermooptical response of only 1.5° C. for each mixture, can act as colorimetric indicator of the temperature differentiation on the surface of the biological objects, on which these mixtures arranged on a fixing carrier, will be placed.

Preferably, the temperature range, in which mesophase formed from each of the three mixtures of liquid-crystal compounds maintains the ability of thermooptical response, cumulatively comprises the range of 31.8° C. to 34.8° C., that is corresponding to the measured in vivo range of the temperatures of the mammary glands surface in women, thus these mixtures are useful to the range imaging (every 0.5° C.) of the isotherm distribution on the surface of the breast. Such imaging of the surface of the breast temperature has the application to the early diagnosis of thermic markers of pathologic processes taking place inside, as well as on the surface of the breast.

The thermochromic response separation of the mesophase every 0.5° C. is possible due to the advantageous use of 4,4'-dipentylazoxybenzene as an admixture, being its new application—to produce the thermooptically active passive mesophase (differently from a case, wherein it is present as a component of the liquid-crystal mixture for the indicators controlled by the field effect, as described in polish patent application PL124264B1, dated 24, Jul. 1979 r., by R. Dabrowski et al.) and allows for unequivocal detection of the examined organ surface areas of the thermic differentiation, at least corresponding to the rated gradient known from the literature (0.7° C.), which is characteristic for the tumours neoplasmic malignant growth type. In particular, it means that the successive application fixed on the carrier first mixture, then second mixture and third mixture, allows the detection of the areas on the examined surface of the breast that are anomalous in respect of thermal characteristic, in whole range of surface temperature experimentally registered for this organ, with simultaneous very easy detection of the focal changes of the temperature due to the fact, that the individual primary colours (red, green, blue) visible as the colour of light reflected in the mesophase formed by given liquid crystals mixture, are observed precisely every 0.5° C.—thus two adjacent areas of different colour may minimally differ from each other by this temperature range.

In first aspect, the present invention relates to the mixtures of the liquid-crystal compounds having the ability to form the thermooptically active thermotropic mesophase in narrow range of temperatures, with the colour transitions changing every 0.5° C.

The liquid-crystal mixtures according to the present invention comprise the following compounds:

cholesteryl pelargonate (chiral nematic) melting at the temperature 80.5° C. to achieve the isotropic liquid state at the temperature 90° C. (temperature of clarification), CAS registry number 633-31-8, and the structure represented by the formula 1;

Formula 1 cholesteryl oleyl carbonate, CAS registry number 17110-51-9, and the structure represented by the formula 2;

Formula 2 cholesteryl propionate, CAS registry number 633-31-8, and the structure represented by the formula 3;

Formula 3

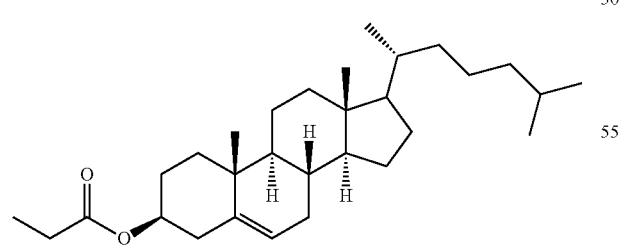

cholesteryl chloride, CAS registry number 910-31-6, and the structure represented by the formula 4;

Formula 4

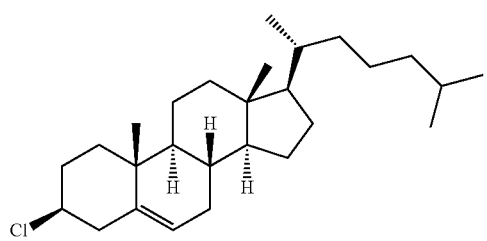

4,4'-dipentylazoxybenzene, CAS registry number 37592-87-3, and the structure represented by the formula 5;

Formula 5

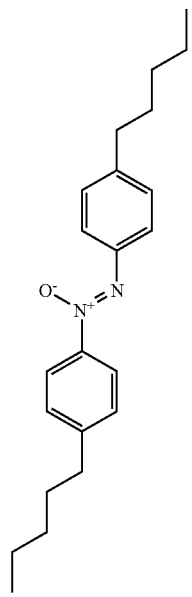

The mixture of liquid-crystal compounds according to the present invention consists of cholesteryl pelargonate in amount from 48.61% to 52.53% by weight, cholesteryl oleyl carbonate in amount from 46.47% to 50.39% by weight, cholesteryl propionate in amount from 0.18% to 0.28% by weight, cholesteryl chloride in amount from 0.16% to 0.20% by weight and 4,4'-dipentylazoxybenzene in amount from 0.52% to 0.66% by weight and forms thermooptically active mesophase in the temperature range from 31.8° C. to 34.8° C.

In one embodiment, the composition in % by weight of the first mixture according to the present invention is as follows:

| | |
|---|---|
| cholesteryl pelargonate | 48.61% |
| cholesteryl oleyl carbonate | 50.39% |
| cholesteryl propionate | 0.28% |
| cholesteryl chloride | 0.20% |
| 4,4'-dipentylazoxybenzene | 0.52%. |

Preferably in the first mixture according to the present invention, the mesophase is thermooptically responsive in the temperature range from 31.8° C. to 32.8° C., wherein at the temperature 31.8° C. appears reflected in the mesophase light of red colour (of wavelength 720 nm) and this colour is maintained through 0.5° C., at the temperature 32.3° C. appears reflected in the mesophase light of green colour (of wavelength 545 nm) and this colour is maintained through 0.5° C., and at the temperature 32.8° C. appears reflected in the mesophase light of blue colour (of wavelength 410 nm) and this colour is maintained through 0.5° C.

In second embodiment, the composition in % by weight of the second mixture according to the present invention is as follows:

| | |
|---|---|
| cholesteryl pelargonate | 50.28% |
| cholesteryl oleyl carbonate | 48.72% |
| cholesteryl propionate | 0.24% |
| cholesteryl chloride | 0.18% |
| 4,4'-dipentylazoxybenzene | 0.58% |

Preferably in the second mixture according to the present invention, the mesophase is thermooptically responsive in the temperature range from 32.8° C. to 33.8° C., wherein at the temperature 32.8° C. appears reflected in the mesophase light of red colour (of wavelength 720 nm) and this colour is maintained through 0.5° C., at the temperature 33.3° C. appears reflected in the mesophase light of green colour (of wavelength 545 nm) and this colour is maintained through 0.5° C., and at the temperature 33.8° C. appears reflected in the mesophase light of blue colour (of wavelength 410 nm) and this colour is maintained through 0.5° C.

In third embodiment, the composition in % by weight of the third mixture according to the present invention is as follows:

| | |
|---|---|
| cholesteryl pelargonate | 52.53% |
| cholesteryl oleyl carbonate | 46.47% |
| cholesteryl propionate | 0.18% |
| cholesteryl chloride | 0.16% |
| 4,4'-dipentylazoxybenzene | 0.66% |

Preferably in the third mixture according to the present invention, the mesophase is thermooptically responsive in the temperature range from 33.8° C. to 34.8° C., at the temperature 33.8° C. appears reflected in the mesophase light of red colour (of wavelength 720 nm) and this colour is maintained through 0.5° C., at the temperature 34.3° C. appears reflected in the mesophase light of green colour (of wavelength 545 nm) and this colour is maintained through 0.5° C., and at the temperature 34.8° C. appears reflected in the mesophase light of blue colour (of wavelength 410 nm) and this colour is maintained through 0.5° C.

With regard for its unique thermooptical properties, the mixtures according to the present invention mentioned above are suitable for the use as active layers in colorimetric detection of temperature differentiation on the surface of the biological objects.

In second aspect, the present invention relates to the system of three liquid-crystal mixtures forming the thermotropic mesophase, which are adapted for imaging of the isotherm distribution on the surface of the biological objects in narrow range of temperatures from 31.8° C. to 34.8° C., maintaining the thermochromic separation for three primary colours of the light selectively reflected in the mesophase—red colour (of wavelength 720 nm), green colour (of wavelength 545 nm) and blue colour (of wavelength 410 nm)—in the 0.5° C. intervals.

Mentioned above system is suitable to the successive applications for the colorimetric detection of temperature differentiation on the surface of the biological objects in narrow range of temperatures from 31.8° C. to 34.8° C., particularly for the pathological lesions imaging in mammary glands in women.

EXAMPLE 1

Preparation of Liquid-Crystal Mixtures

Using analytical balance, the individual components of the liquid-crystal mixtures was weighted. The compositions of the mixtures are presented in Table 1.

TABLE 1

| Chemical compound | Mixture I | Mixture II | Mixture III |
|---|---|---|---|
| cholesteryl pelargonate | 48.61 g | 50.28 g | 52.53 g |
| cholesteryl oleyl carbonate | 50.39 g | 48.72 g | 46.47 g |
| cholesteryl propionate | 0.28 g | 0.24 g | 0.18 g |
| cholesteryl chloride | 0.20 g | 0.18 g | 0.16 g |
| 4,4'-dipentylazoxybenzene | 0.52 g | 0.58 g | 0.66 g |

Weighted samples of the individual mixtures components were placed in 200 ml Beakers. The mixtures were heated at the temperature about 70° C. with mixing by the use of mechanical stirrer RD 50D type for about 24 hours to obtain the homogenous mixture.

The obtained liquid-crystal mixtures were made to control in order to check the temperature phase transitions. The sample of the melted mixture was applied on a blackened metal plate of dimensions 50 mm×50 mm of a cooling-heating table with electronically stabilised preheating from Semic, equipped with programmable temperature controller from Shimano. The sample of the mixture was illuminated with a light source D65 (imitation of the white light), wherein the light source was placed in a holders assembly providing stable geometry of the colour response measurements. The sample of the mixture was cooled down to determined temperatures and visually checked for the colour response.

For the mixture I:
at the temperature 31.8° C.-32.3° C. reflected light of red colour (720 nm);
at the temperature 32.3° C.-32.8° C. reflected light of green colour (545 nm);

at the temperature 32.8° C.-33.3° C. reflected light of blue colour (410 nm) were obtained.

For the mixture II:

at the temperature 32.8° C.-33.3° C. reflected light of red colour (720 nm);

at the temperature 33.3° C.-33.8° C. reflected light of green colour (545 nm);

at the temperature 33.8° C.-34.3° C. reflected light of blue colour (410 nm) were obtained.

For the mixture III:

at the temperature 33.8° C.-34.3° C. reflected light of red colour (720 nm);

at the temperature 34.3° C.-34.8° C. reflected light of green colour (545 nm);

at the temperature 34.8° C.-35.3° C. reflected light of blue colour (410 nm) were obtained.

EXAMPLE 2

Preparation of the plate containing the mixture III according to the example 1, for the use as themodetector.

On the rectangular plate surface made of transparent organic polymer, e.g. polycarbonate or polyester, was applied an adhesive coating, e.g. aqueous dispersion of acrylonitrile copolymer, then dried at the temperature 80° C. for about 2 hours. Next, on the adhesive coating such prepared the liquid-crystal mixture I according to the example 1, suspended in aqueous dispersion of polyvinyl alcohol was applied by means of squeegees. The layer of the liquid crystals, after pre-evaporation of the dispersing component by placing the plate functioning as a carrier for the liquid crystals under an infrared radiator at the temperature 280° C. for 30 minutes, was coated with an encapsulating layer of vinyl polymer. Polymerisation process was carried out in the conditions of relative humidity not lower than 80% and at the temperature of 25° C., for about 12 hours. When the polymerisation process was complete, the transparent coated with liquid crystals plate was coated with the absorptive coating containing black organic pigment from the vinyl polymer side using a screen printing technique. When the absorptive coating was dried (about 12 hours at the temperature of 25° C.), the plate containing the liquid-crystal mixture III was obtained, showing the thermooptical response in the temperature range from 33.8° C. to 34.8° C., ready to use as the thermodetector for imaging of the isotherm distribution on the surface of the examined mammary gland.

The invention claimed is:

1. A method of diagnosing pathological lesions of the mammary gland by means of thermography, wherein one or more temperature anomalies resulting from said pathological lesions are detected by thermography on the breast surface every 0.5° C. in the temperature range from 31.8° C. to 34.8° C., beginning at 31.8° C. and divided into three sub-ranges: from 31.8° C. to 32.8° C., from 32.8° C. to 33.8° C. and from 33.8° C. to 34.8° C., wherein the temperature detection is carried out using three liquid-crystal mixtures able to form a thermooptically active mesophase every 0.5° C. in the three temperature ranges from 31.8° C. to 32.8° C., from 32.8° C. to 33.8° C. and from 33.8° C. to 34.8° C., wherein the first mixture forms thermooptically active mesophase in the temperature range from 31.8° C. to 32.8° C. and the first mixture consists of 48.61% by weight cholesteryl pelargonate, 50.39% by weight cholesteryl oleyl carbonate, 0.28% by weight cholesterol propionate, 0.20% by weight cholesterol chloride and 0.52% by weight 4,4'-dipentylazoxybenzene, the second mixture forms thermooptically active mesophase in the temperature range from 32.8° C. to 33.8° C. and the second mixture consists of 50.28% by weight cholesteryl pelargonate, 48.72% by weight cholesteryl oleyl carbonate, 0.24% by weight cholesteryl propionate, 0.18% by weight cholesteryl chloride and 0.58% by weight 4,4'-dipentylazoxybenzene', the third mixture forms thermooptically active mesophase in the temperature range from 33.8° C. to 34.8° C. and the third mixture consists of 52.53% by weight cholesteryl pelargonate, 46.47% by weight cholesterol oleyl carbonate, 0.18% by weight cholesterol propionate, 0.16% by weight cholesterol chloride and 0.66% by weight 4,4'-dipentylazoxybenzene.

2. The method according to claim 1, wherein said three liquid-crystal mixtures are arranged separately on a fixing carrier.

3. The method according to claim 2, comprising steps of successive application fixed on a carrier of the first mixture, then the second mixture, and the third mixture.

* * * * *